(12) United States Patent
Liberman et al.

(10) Patent No.: US 10,595,828 B2
(45) Date of Patent: Mar. 24, 2020

(54) PROBE, ULTRASOUND IMAGING APPARATUS AND CONTROLLING METHOD OF THE ULTRASOUND IMAGING APPARATUS

(71) Applicant: SAMSUNG ELECTRONICS CO., LTD., Suwon-si (KR)

(72) Inventors: Alexander Liberman, San Diego, CA (US); Andrew C. Kummel, San Diego, CA (US); James Wang, San Diego, CA (US); Sarah L. Blair, La Jolla, CA (US); William C. Trogler, San Diego, CA (US); Hotaik Lee, Yongin-si (KR)

(73) Assignees: SAMSUNG ELECTRONICS CO., LTD., Suwon-si (KR); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1126 days.

(21) Appl. No.: 14/918,004

(22) Filed: Oct. 20, 2015

(65) Prior Publication Data
US 2016/0143624 A1    May 26, 2016

(30) Foreign Application Priority Data
Nov. 26, 2014 (KR) .......................... 10-2014-0166059

(51) Int. Cl.
*A61B 8/08* (2006.01)
*A61B 8/00* (2006.01)
(Continued)

(52) U.S. Cl.
CPC ............ *A61B 8/5207* (2013.01); *A61B 8/085* (2013.01); *A61B 8/481* (2013.01); *A61B 8/54* (2013.01);
(Continued)

(58) Field of Classification Search
CPC ....... A61B 8/5207; A61B 8/085; A61B 8/481; A61B 8/54; A61B 8/4405; A61B 8/14;
(Continued)

(56) References Cited

U.S. PATENT DOCUMENTS

| 5,833,613 A * | 11/1998 | Averkiou ................. A61B 8/06 600/440 |
| 2005/0038340 A1 * | 2/2005 | Vaezy ...................... A61B 8/06 600/439 |

(Continued)

*Primary Examiner* — Peter Luong
(74) *Attorney, Agent, or Firm* — Sughrue Mion, PLLC

(57) ABSTRACT

Disclosed herein is an ultrasound imaging apparatus and a controlling method thereof. The ultrasound imaging apparatus includes a controller configured to generate a control signal to control an operation of a probe, and a transceiver configured to transmit the control signal to the probe and to receive a signal transmitted from the probe. The controller may control the operation of the probe so that the probe may irradiate focused ultrasound energy when contrast agents composed of a silica nanostructure are injected into an object, and the controller may control the operation of the probe so that the probe may irradiate diagnostic ultrasound energy when the focused ultrasound energy is irradiated.

14 Claims, 31 Drawing Sheets
(2 of 31 Drawing Sheet(s) Filed in Color)

(51) Int. Cl.
*A61N 7/02* (2006.01)
*A61B 8/14* (2006.01)
*A61N 7/00* (2006.01)

(52) U.S. Cl.
CPC .................. *A61N 7/02* (2013.01); *A61B 8/14* (2013.01); *A61B 8/4405* (2013.01); *A61B 8/463* (2013.01); *A61B 8/5246* (2013.01); *A61N 2007/0039* (2013.01); *A61N 2007/0052* (2013.01)

(58) Field of Classification Search
CPC ........ A61B 8/463; A61B 8/5246; A61N 7/02; A61N 2007/0039; A61N 2007/0052
See application file for complete search history.

(56) References Cited

U.S. PATENT DOCUMENTS

| | | | |
|---|---|---|---|
| 2006/0293598 A1* | 12/2006 | Fraser ...................... | A61B 8/08 600/439 |
| 2008/0097207 A1* | 4/2008 | Cai .......................... | A61B 8/08 600/442 |
| 2009/0187106 A1* | 7/2009 | Lee ......................... | A61B 8/481 600/458 |
| 2012/0128221 A1* | 5/2012 | Lazebnik ............... | A61B 8/463 382/131 |
| 2012/0323112 A1* | 12/2012 | Jokerst ................... | A61B 8/481 600/420 |
| 2014/0213841 A1* | 7/2014 | D'Hooge ............... | A61B 8/481 600/1 |

* cited by examiner

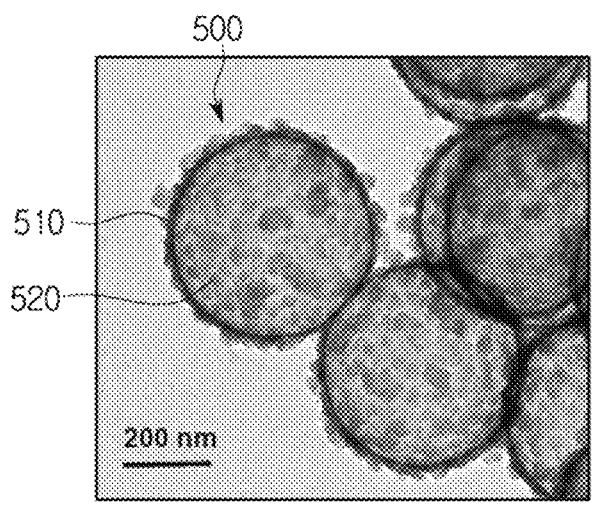

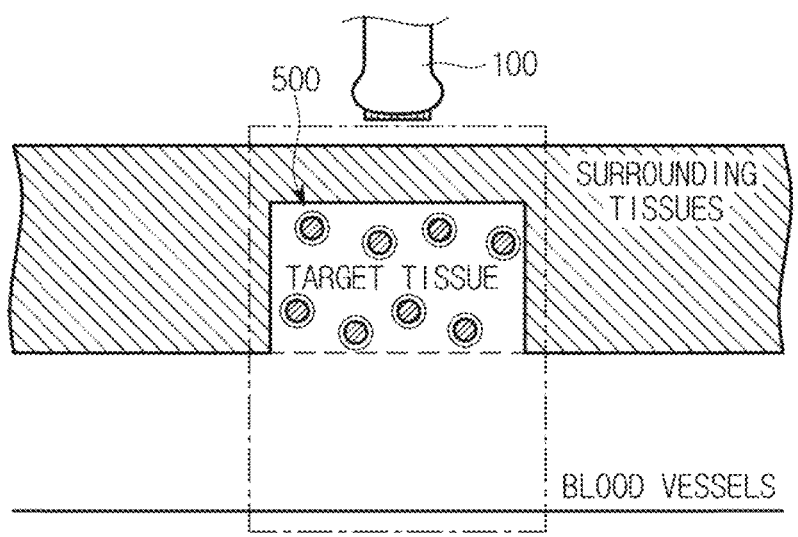

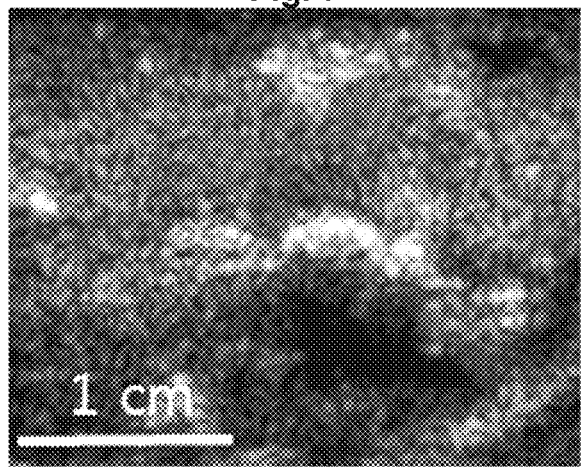

PROBE, ULTRASOUND IMAGING APPARATUS AND CONTROLLING METHOD OF THE ULTRASOUND IMAGING APPARATUS

CROSS-REFERENCE TO RELATED APPLICATION(S)

This application claims priority from Korean Patent Application No. 10-2014-0166059, filed on Nov. 26, 2014 in the Korean Intellectual Property Office, the disclosure of which is incorporated herein by reference in its entirety.

BACKGROUND

1. Field

Exemplary embodiments relate to a probe that is configured to transmit and receive ultrasound energy, an ultrasound imaging apparatus that is configured to generate an ultrasonic image, and a control method of the ultrasound imaging apparatus.

2. Description of Related Art

An ultrasound imaging apparatus irradiates ultrasound energy to a target part in an object through the surface of the object, detects echo ultrasound energy reflected from the object and then noninvasively provides images about an examined part, such as a tomogram of a soft tissue or bloodstream.

The ultrasound imaging apparatus is compact, inexpensive, and capable of displaying a diagnostic imaging immediately, as compared with another type of diagnostic imaging apparatus, e.g., X-ray device, Computerized Tomography (CT) scanner, Magnetic Resonance Image (MRI), diagnostic nuclear medical apparatus. In addition, the ultrasound imaging apparatus is safe because there is no risk of radiation exposure. Therefore, the ultrasound imaging apparatus is widely used in medical examination at maternity, cardiology, abdomen, and urology clinics.

To acquire images of the inside of an object, the ultrasound imaging apparatus may include an ultrasonic probe configured to irradiate ultrasound energy to the object and to receive echo ultrasound energy reflected from the object, and a main body configured to generate an ultrasonic image.

When examining an object using an ultrasound imaging apparatus, contrast agents may be used. The contrast agents may be injected into a blood vessel in the object, and may stably act with the ultrasound energy while circulating in the blood vessel.

A probe may receive echo ultrasound energy reflected by the object in which the ultrasonic contrast agent is injected, and may convert the echo ultrasound energy into an electrical signal. A main body may generate contrast agent images to detect an area in which the contrast agents are injected, based on the electrical signal outputted from the probe.

SUMMARY

Therefore, it is an aspect of one or more exemplary embodiments to provide an ultrasound imaging apparatus capable of generating a contrast agent image to detect contrast agents injected into an object, generating a diagnostic image to diagnose inside the object, and generating a combined image of the contrast agent image and the diagnostic image, and a control method of the ultrasound imaging apparatus.

It is another aspect of one or more exemplary embodiments to provide a probe that is capable of irradiating focused ultrasound energy to activate contrast agents, detecting the contrast agents, and receiving echo ultrasound energy to diagnose inside an object.

Additional aspects will be set forth in part in the description which follows and, in part, will be apparent from the description, or may be learned by practice of the exemplary embodiments.

In accordance with one aspect, an ultrasound imaging apparatus includes a controller configured to generate a control signal to control an operation of a probe, and a transceiver configured to transmit the control signal to the probe and to receive a signal transmitted from the probe, wherein the controller may be further configured to control the operation of the probe so that the probe may irradiate focused ultrasound energy when at least one contrast agent composed of a silica nanostructure is injected into an object, and the controller may be further configured to control the operation of the probe so that the probe may irradiate diagnostic ultrasound energy when the focused ultrasound energy is irradiated.

The controller may be further configured to control the operation of the probe so that high intensity focused ultrasound (HIFU) energy may be irradiated as the focused ultrasound energy.

The controller may be further configured to control the operation of the probe so that echo ultrasound energy reflected from an object may be received when the diagnostic ultrasound energy is irradiated.

The ultrasound imaging apparatus may further include an image processor configured to generate an ultrasound image based on an electrical signal when the transceiver receives the electrical signal that corresponds to the echo ultrasound energy.

The image processor may be further configured to generate a contrast agent image and an internal diagnostic image according to a set diagnostic mode.

The image processor may be further configured to generate a combined image by combining the contrast agent image with the internal diagnostic image.

The ultrasound imaging apparatus may further include a display configured to display the combined image.

The image processor may be further configured to extract a target tissue from the contrast agent image and to combine the target tissue with the internal diagnostic image.

The image processor may be further configured to generate a volume rendering image of the target tissue.

The image processor may be further configured to detect a target tissue from the contrast agent image and to detect at least one surrounding tissue from the internal diagnostic image, and to combine a contrast agent image of the target tissue with an internal diagnostic image of the at least one surrounding tissue.

The image processor may be further configured to perform an image post-processing operation with respect to the contrast agent image and the internal diagnostic image.

The image post-processing operation may include correcting or readjusting at least one from among a contrast, a brightness and a sharpness in each of the contrast agent image and the internal diagnostic image.

The image processor may be further configured to generate a Cadence Pulse Sequencing mode (CPS-mode) image as a contrast agent image, and a Brightness mode (B-mode) image as an internal diagnostic image.

The ultrasound imaging apparatus may further include an input device configured to receive a selection of an image mode from a user, wherein the image processor may be further configured to generate the contrast agent image when a first image mode is selected, and to generate the internal diagnostic image when a second image mode is selected.

The display may be further configured to display diagnosis data related to the target tissue.

The ultrasound imaging apparatus may further include an input device configured to receive a magnification of the combined image from a user, wherein the display may be further configured to display a target point that is enlarged or reduced according to the received magnification.

The at least one contrast agent may include a shell composed of a silica nanostructure, and a core composed of a liquid perfluorocarbon or a gas perfluorocarbon.

A size of the shell may be equal to or greater than 10 nanometers and equal to or less than 3000 nanometers.

In accordance with another aspect, a probe includes a transducer configured to activate at least one contrast agent by irradiating focused ultrasound energy toward an object when the at least one contrast agent composed of a silica nanostructure is injected into the object, and to irradiate diagnostic ultrasound energy toward the object when the focused ultrasound energy is irradiated, and a transceiver configured to receive a control signal to control the transducer.

In accordance with another aspect, a control method which is executable by using an ultrasound imaging apparatus includes controlling an operation of a probe to irradiate focused ultrasound energy when at least one contrast agent composed of a silica nanostructure is injected into an object, and controlling an operation of the probe to irradiate diagnostic ultrasound energy when the focused ultrasound energy is irradiated.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and/or other aspects will become apparent and more readily appreciated from the following description of exemplary embodiments, taken in conjunction with the accompanying drawings of which:

FIGS. 3B and 3C are captured images of contrast agents;

FIGS. 5A, 5B, 6A, and 6B are views illustrating a process of activating contrast agents injected into a target tissue;

FIG. 7 is a view illustrating a B-mode image generated by an imaging processor;

DETAILED DESCRIPTION

Figure 1:
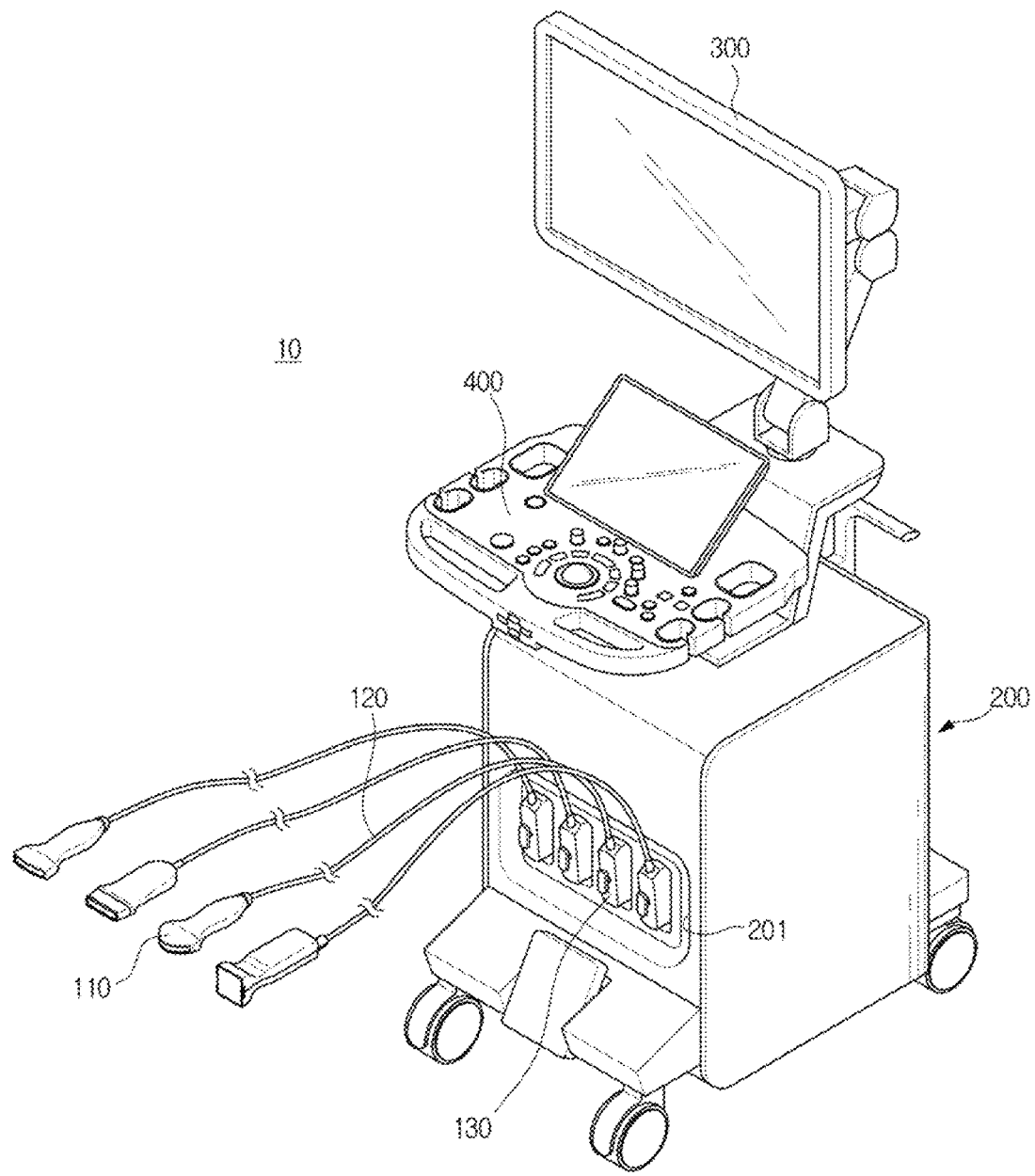
FIG. 1 is a perspective view illustrating an ultrasound imaging apparatus, in accordance with an exemplary embodiment.

The present inventive concept will now be described more fully with reference to the accompanying drawings, in which exemplary embodiments are shown. The present inventive concept may, however, be embodied in many different forms and should not be construed as being limited to the exemplary embodiments set forth herein; rather, these exemplary embodiments are provided so that this disclosure will be thorough and complete, and will fully convey the present inventive concept to those of skill in the art. Like reference numerals in the drawings denote like elements, and thus their description will be omitted. In the description, if it is determined that a detailed description of commonly-used technologies or structures related to the exemplary embodiments may unnecessarily obscure the subject matter of the exemplary embodiments, the detailed description will be omitted. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

Exemplary embodiments will now be described with reference to accompanying drawings.

Figure 2:
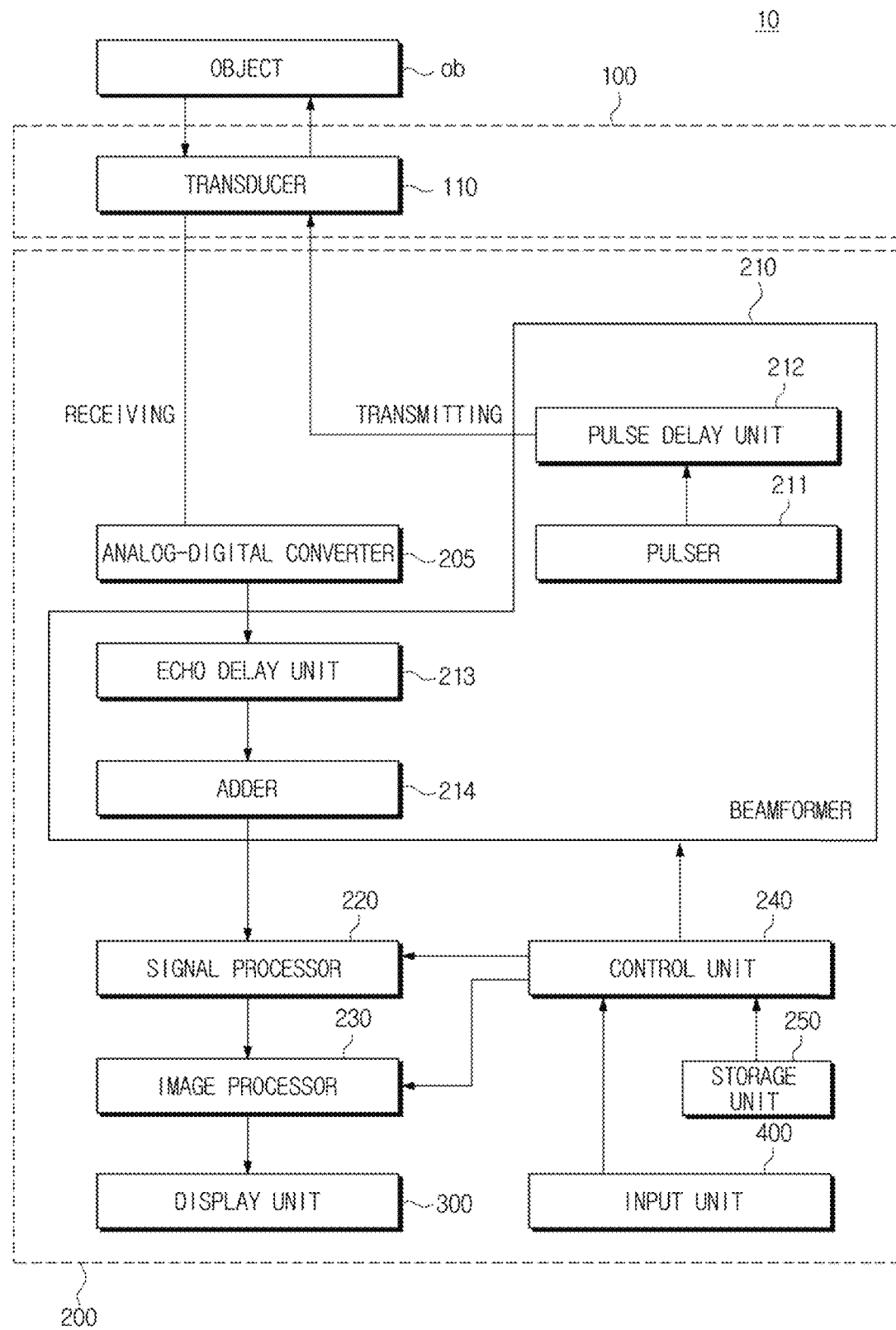
FIG. 2 is a control block diagram illustrating the ultrasound imaging apparatus, in accordance with an exemplary embodiment.

FIG. 1 is a perspective view illustrating an ultrasound imaging apparatus, in accordance with an exemplary embodiment, and FIG. 2 is a control block diagram illustrating the ultrasound imaging apparatus, in accordance with an exemplary embodiment.

As illustrated in FIGS. 1 and 2, an ultrasound imaging apparatus 10 may include a probe 100, and a main body 200. The main body 200 may include an analog-digital converter 205, a beamformer 210, a signal processor 220, an image processor 230, a control unit (also referred to herein as a "controller") 240, a storage unit (also referred to herein as a "storage device" and/or as a "storage") 250, a display unit (also referred to herein as a "display device" and/or as a "display") 300 and an input unit (also referred to herein as an "input device") 400.

Hereinafter the probe 100 provided in the ultrasound imaging apparatus 10 will be described.

The probe 100 may include at least one transducer 110, and may be configured to irradiate focused ultrasound energy and diagnostic ultrasound energy toward an object. The probe 100 may be configured to receive echo ultrasound energy reflected from the object, and to convert the received ultrasound energy into an electrical signal or vice versa.

An object may include any of a living body of a human or animal, tissues in the living body, such as blood vessels, bones, muscles, etc., but is not limited thereto. Therefore, anything whose internal structure may be imaged by the ultrasound imaging apparatus 10 may be the object.

Diagnostic ultrasound energy may represent ultrasound energy irradiated from the probe 100 in order to generate diagnostic images used to examine or diagnose the inside of an object ob according to a diagnostic mode selected by the main body 200, or in order to generate a contrast agent image used to detect contrast agents injected into a target tissue.

A diagnostic mode may include an Amplitude mode (A-mode), a Brightness mode (B-mode), a Doppler mode (D-mode), an Elastography mode (E-mode), a Motion mode (M-mode), and a Cadence Pulse Sequencing mode (CPS-mode), but is not limited thereto. The diagnostic mode may include a mode (hereinafter referred to as a combined mode) to generate an image that combines two or more images of an A-mode, a B-mode, a D-mode, an E-mode, a M-mode, and a CPS-mode.

The diagnostic ultrasound energy may have different frequency bands or energy intensities with respect to each other according to the diagnostic mode.

In comparison with the diagnostic ultrasound energy, focused ultrasound energy may be a single pulse having a short time to be applied and being applied by focused at a target point. For example, the focused ultrasound energy may have a pulse width of greater than 20 microseconds ($\mu s$) and less than 50 $\mu s$, and may have a center frequency of greater than 800 kHz. The focused ultrasound energy may be realized by high intensity focused ultrasound (HIFU) energy, and may generate an energy intensity that is greater than 3 MPa at a target point. The focused ultrasound energy may generate heat at the target point by applying a high energy intensity to the target point. Hereinafter high intensity focused ultrasound energy will be described as an example of focused ultrasound energy.

The focused ultrasound energy may be irradiated toward the object ob to activate one or more contrast agents, which will be described below with reference with FIGS. 3 and 4.

Echo ultrasound energy may represent ultrasonic waves reflected from an object ob upon which diagnostic ultrasound energy is irradiated, and may have various frequency bands and various energy intensities to generate various ultrasound images according to the diagnostic mode.

Figure 3A:
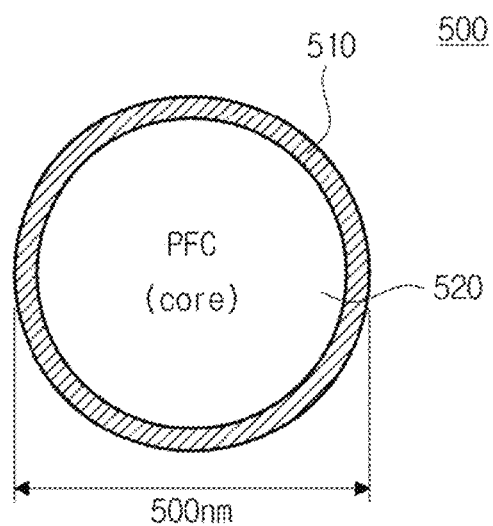
FIG. 3A is a schematic view illustrating a structure of contrast agents.
Figure 3C:
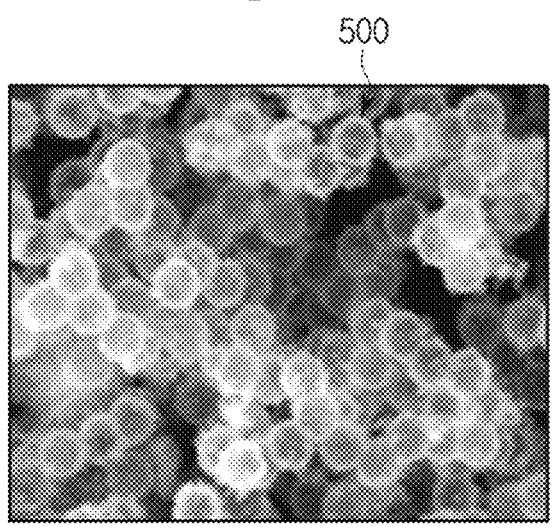

Contrast agent is a material that reacts to ultrasound energy and may be injected into a blood vessel (e.g., vein) of the object ob. Hereinafter a structure of contrast agents will be described with reference with FIGS. 3A and 3B. FIG. 3A is a schematic view illustrating a structure of contrast agents, and FIGS. 3B and 3C are captured images of contrast agents.

Referring to FIGS. 3A and 3B, a contrast agent 500 may include a shell 510 and a core 520. The shell 510 may be formed of a material having biocompatibility and may surround core material. The core 520 may be formed of a material which generates echo ultrasound energy that has stronger reflectance than that of a surrounding by reacting to incident ultrasound energy.

For example, as illustrated in FIG. 3A, the contrast agent 500 may include the shell 510 composed of a silica nanostructure, and the core 520 composed of a perfluorocarbon (PFC).

The shell 510 composed of a silica nanostructure may have a diameter which is greater than 10 nanometers (nm) and less than 3000 nm, e.g., a diameter that is smaller than that of blood vessels in the vicinity of a tumor and greater than that of normal blood vessels. Accordingly, the shell 510 composed of a silica nanostructure may permeate a tumor via blood vessels near the tumor that are looser than normal blood vessels, so that the shell 510 may be selectively stored on a target tissue, such as a tumor and a cancer.

The shell 510 composed of a silica nanostructure may not be discharged through a liver and kidneys or may not be evaporated through lungs. Accordingly, the shell 510 composed of a silica nanostructure may have a high stability and a long residence time in a living body.

The transducer 110, according to an exemplary embodiment, may dissolve the shell 510 by irradiating high intensity focused ultrasound energy to the shell 510 composed of a silica nanostructure, and thus the core 520 surrounded by the shell 510 may be scattered.

For example, the transducer 110 may dissolve the shell 510 by irradiating high intensity focused ultrasound energy to the shell 510 of the contrast agent 500, which is stacked on a target tissue, such as a tumor and a cancer, according to a control signal received from the main body 200, and thus the core 520 surrounded by the shell 510 may be scattered in the target tissue.

The core 520 may include either or both of a liquid perfluorocarbon (liquid PFC) and a gas perfluorocarbon (gas PFC). A perfluorocarbon has a low viscosity, a low surface tension, a good spreadability (low attractive force), a high fluidity, a low dielectric constant, a high vapor pressure, a high compressibility and a high gas solubility. In addition, a perfluorocarbon may have a high density, antifriction properties, and magnetic susceptibility values. Perfluorocarbons are generally not harmful to human body, even in relatively large amounts thereof. Pure perfluorocarbons having a molecular weight within a range from 460 Da to 520 Da may be nonpoisonous and may not cause cancers, mutation, malformation, and an immune reaction.

A perfluorocarbon may include a perfluorochemical having one end terminal selected from a group including thiol, phosphine and phosphine oxide, or amphiphilic fluorinated hydrocarbon, and may include any one selected from among a group including perfluorinated alcohol phosphate ester and salt thereof, perfluorinated sulfonamide alcohol phosphate ester and salt thereof, perfluorinated alkyl sulfonamide alkylene quaternary ammonium salt, N,N-(carboxyl-substituted lower alkyl) perfluorinated alkyl sulfonamide, and a mixture thereof, but is not limited thereto.

In this case, perfluorinated alcohol phosphate ester may include mono- or bis-(1H,1H,2H,2H-perfluoroalkyl phosphate)-derived free acid of diethanolamine salt.

A perfluorinated sulfonamide alcohol phosphate ester may include any one selected from among a group including perfluoro-n-octyl-Nethysulfonamidoethyl phosphate, bis (perfluoro-n-octyl-N-ethylsulfonamidoethyl) phosphate, the ammonium salt of bis(perfluoro-n-octyl-N-ethylsulfonamidoethyl)phosphate, bis(perfluorodecyl-N-ethylsulfonamidoethyl)phosphate, and bis(perfluorohexy-N-ethylsulfonamidoethyl)phosphate, but is not limited thereto.

A gas perfluorocarbon may have a strong reflectance against ultrasound energy. Therefore, when the gas perfluorocarbon is injected into a target tissue, diagnostic ultrasound energy irradiated from the transducer 110 may be reflected from the target tissue as echo ultrasound energy that has a high energy intensity while being reflected in a nonlinear manner due to a variable reflectance from a surrounding tissue. The echo ultrasound energy reflected in a nonlinear manner may have harmonic content.

When the transducer 110 acquires echo ultrasound energy that has a high energy intensity from the target tissue, the main body 200 may generate ultrasound images having high contrast due to a variable reflectance from a surrounding tissue. When the transducer 110 acquires echo ultrasound energy that includes harmonic content, the main body 200 may generate high resolution ultrasound images in comparison with acquiring basic frequency content. A gas perfluorocarbon injected into a target tissue will be described below with reference with FIG. 5.

Meanwhile, when the core 520 is composed of a liquid perfluorocarbon, the transducer 110 according to an exemplary embodiment may irradiate high intensity focused ultrasound energy to the core 510 so that the liquid perfluorocarbon may be evaporated.

In this case, the transducer 110 may dissolve the shell 510 and evaporate liquid perfluorocarbon by irradiating high intensity focused ultrasound energy to the contrast agents 500 including the shell 510 composed of a silica nanostructure, and thus the core 520 surrounded by the shell 510 may be scattered and may be activated to be a gas perfluorocarbon.

Hereinafter, a process of activating the contrast agents 500 will be described in detail with reference with FIGS. 4A, 4B, and 4C.

Figure 4A:
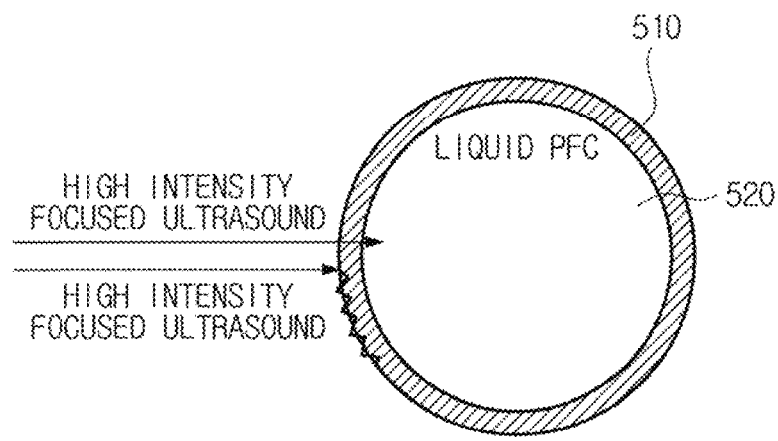
FIGS. 4A, 4B, and 4C are views illustrating a process of activating contrast agents by using ultrasound energy irradiated from a transducer.
Figure 4B:
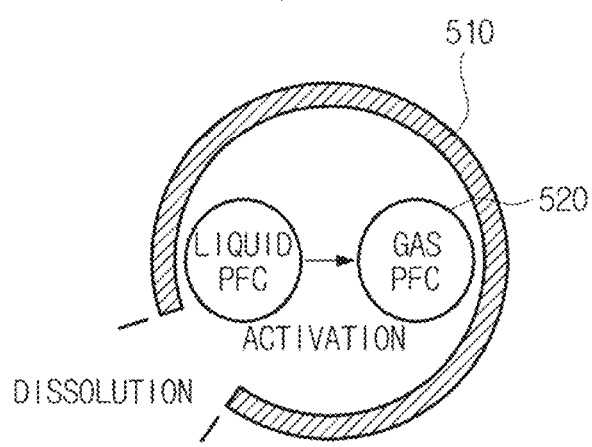
Figure 4C:
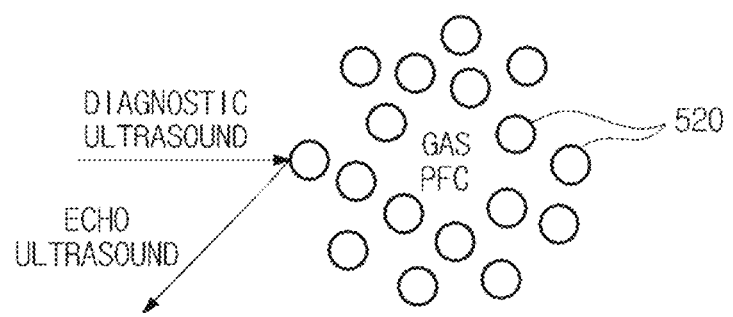

FIGS. 4A, 4B, and 4C are views illustrating a process of activating contrast agents by using ultrasound energy irradiated from a transducer. As illustrated in FIGS. 4A, 4B, and 4C, the core 520 composed of a liquid perfluorocarbon will be described, but is not limited thereto. The core 520 may be composed of a gas perfluorocarbon.

As illustrated in FIG. 4A, when the transducer 110 irradiates high intensity focused ultrasound energy to the contrast agents 500, the shell 510 composed of a silica nanostructure may be dissolved and the core 520 composed of a liquid perfluorocarbon may be evaporated into a gas perfluorocarbon, wherein the shell 510 and the core 520 are included in the contrast agents 500. Accordingly, the contrast agents 500 may be activated.

As illustrated in FIG. 4C, when the transducer 110 irradiates diagnostic ultrasound energy to the contrast agents 500, the diagnostic ultrasound may be reflected by the gas perfluorocarbon (echo ultrasound energy may be generated).

In this case, the gas perfluorocarbon may include many bubbles so that the ultrasound energy may be reflected in various directions when the diagnostic ultrasound energy is irradiated.

When the gas perfluorocarbon is injected into the target tissue, the target tissue may generate echo ultrasound energy that includes a higher energy intensity and a nonlinear content in comparison with the surrounding tissue.

FIGS. 5A, 5B, 6A, and 6B are views illustrating a process of activating contrast agents injected into a target tissue.

Figure 5A:
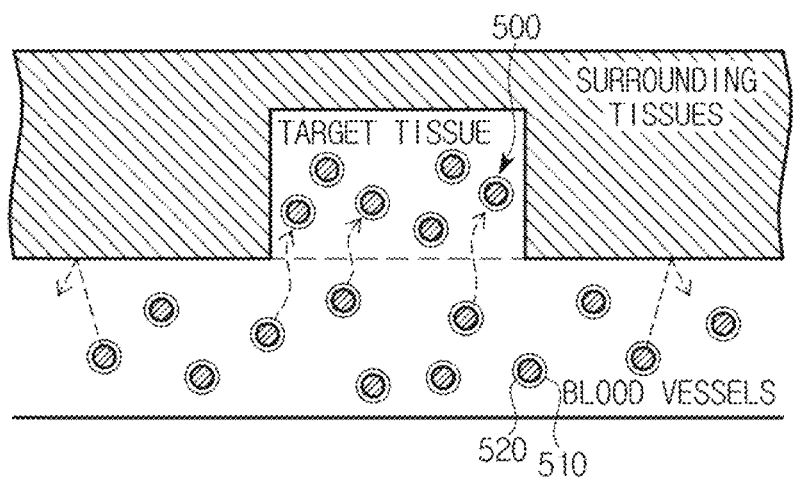

Referring to FIG. 5A, the contrast agents 500, which include the shell 510 composed of a silica nanostructure and the core 520 composed of a liquid perfluorocarbon, may remain without deformation during a certain period of time after injected into blood vessels of an object ob so as to be introduced to a target tissue, such as a tumor and a cancer, from the surrounding tissues.

Figure 6A:
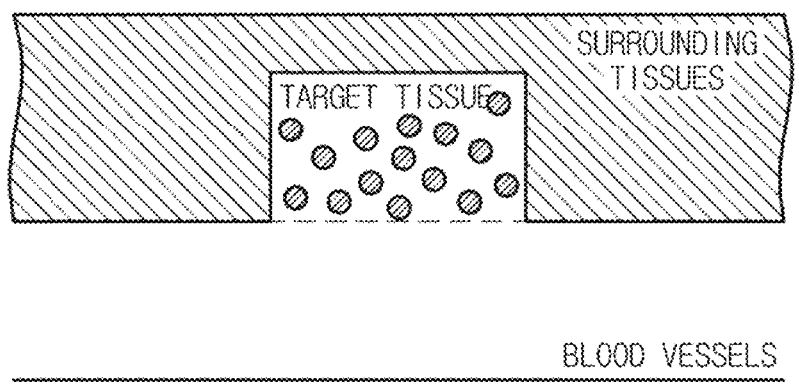

As illustrated in FIG. 5B, when the transducer 110 irradiates high intensity focused ultrasound energy to a target tissue according to a control signal of the main body 200, the shells 510 of the contrast agents 500 may be dissolved and liquid perfluorocarbon may be evaporated so that the contrast agents 500 may be activated, as illustrated in FIG. 6A.

In this case, the transducer 110 may be supplied with a current from an external power supply or an internal electricity storage device, e.g., a battery, and may generate high intensity focused ultrasound energy, which is focused and irradiated to a target tissue, while causing vibrations in transducer elements (not shown) provided in the transducer 110 according to a first control signal of the main body 200.

Figure 6B:
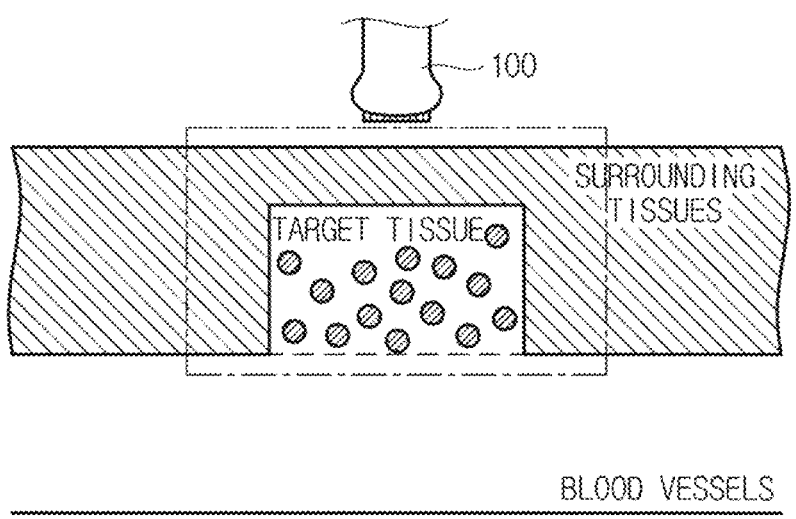

As illustrated in FIG. 6B, the transducer 110 may irradiate diagnostic ultrasound energy to a target tissue and surrounding tissues, and may receive echo ultrasound energy reflected from the target tissue and the surrounding tissues. The transducer 110 may convert the echo ultrasound energy into an electrical signal, and the electrical signal may be transmitted to the main body 200 via cables and male connectors of the probe 100 of FIG. 1.

In particular, the transducer 110 may generate diagnostic ultrasound energy which is irradiated to the surrounding tissues and the target tissue while causing vibrations in transducer elements provided in the transducer 110 according to a second control signal of the main body 200.

Each transducer element may receive again echo ultrasound energy reflected from the surrounding tissues and the target tissue in the object ob by the diagnostic ultrasound energy, and may generate a current having frequency corresponding to a vibration frequency while vibrating according to received echo ultrasound energy.

The transducer 110 may include any of a Magnetostrictive Ultrasonic Transducer (MUT) that uses magnetostrictive effects of a magnetic substance, a Piezoelectric Ultrasonic Transducer (PUT) that uses piezoelectric effects of a piezoelectric substance, piezoelectric micromachined ultrasonic transducer, (pMUT), and/or a Capacitive Micromachined Ultrasonic Transducer (cMUT) that transmits and receives ultrasound energy using vibrations of several hundreds or thousands of micromachined thin films.

The transducer 100 may include any of linear array, convex array, phased array, sector array transducers, etc., which may be arranged in a form of a row or a matrix. When the transducer 110 is arranged in a row, it may be swung in the elevation direction to obtain multiple ultrasound images; and when it is arranged in a form of a matrix, multiple ultrasound images may be obtained from a single transmission of ultrasound energy.

However, the transducer 110 is not limited thereto, and may be implemented with any other types of transducers known to persons of ordinary skill in the art.

Referring again to FIG. 1, the probe 100 may further include a cable 120 and a male connector 130.

One end of the cable 120 may be connected to the transducer 110, and the other end of the cable may be connected to the male connector so that the cable 120 may connect the transducer 110 to the male connector 130.

The male connector 130 may be physically coupled to a female connector 201 of the main body 200 by being connected to the other end of the cable.

The male connector 130 may act as a transmitting/receiving unit (also referred to herein as a "transceiver") configured for transmitting an electrical signal generated by the transducer 110 to the female connector 201 physically coupled thereto, and/or for receiving a control signal generated by the main body 200 from the female connector 201.

However, when the probe 100 is realized by a wireless probe 110, the cable 120 and the male connector 130 may be omitted, and a separated wireless communication module (not shown) provided in the probe 100 may act as the transmitting/receiving unit. Therefore, a type of the probe 100 may be not limited to the probe 100 of FIG. 1.

Hereinafter the main body 200 will be described with reference with FIGS. 1 and 2.

As illustrated in FIG. 1, the main body 200 may be realized by a work station connected to the probe 100 and provided with the display unit 200 and the input unit 400.

The main body 200 may accommodate a primary component of the ultrasound imaging apparatus 10, such as the beamformer 210. When a user inputs an ultrasonic diagnosis command according to a diagnostic mode, the main body 200 may generate a control signal and transmit the control signal to the probe 100.

Hereinafter each component placed or provided in the main body 200 will be described. Referring to FIG. 2, the main body 200, according to an exemplary embodiment, may include the female connector 201, the analog-digital converter 205, the beamformer 210, the image processor 230, the control unit 240, and the storage unit 250.

The female connector 201 may act as a transmitting/receiving unit (also referred to herein as a "transceiver") of the main body 200 which is configured to transmit and/or receive a signal generated by the female connector 201 and the probe 100 to each other. For this purpose, the main body 200 may include one or more the female connector 201 and the female connector 201 may be connected to the probe 100 via the cable 120 and the male connector 130.

The analog-digital converter 205 may be configured to convert an analog signal outputted from the transducer 110 into a digital signal.

The beamformer 210 may include a pulser 211 which is configured for generating alternating current (AC) energy (i.e., a pulse) to drive the transducer 110, a pulse delay unit (also referred to herein as a "pulse delayer") 122 configured for forming a transmission signal pattern by applying a delay time to a pulse according to an ultrasound focal point and a steering angle, an echo delay unit (also referred to herein as an "echo delayer") 213 configured for applying a delay time to a digital signal of each of transducer elements provided in the transducer according to an ultrasound focal point and a steering angle, and an adder 127 configured for adding a time-delayed digital signal of each of the transducer elements.

Hereinafter components included in the beamformer 210 will be described.

The number of the pulser 211 may correspond to the number of transducer elements provided in the transducer 110.

For example, the pulser 211 may generate voltage pulses having widths ranging from −80 V to +80 V or from 0 V or 200 V as a transmission pulse, and may input the voltage pulse to each of the transducer elements provided in the transducer 110. Accordingly the transducer 110 may irradiate focused ultrasound energy and diagnostic ultrasound energy.

The number of the pulse delay unit 212 may correspond to the number of transducer elements provided in the transducer 110.

The pulse delay unit 212 may apply a delay time to each of the transducer elements so that each of the pulses generated by the pulser 211 may reach a focal point. In this case, the focal point may be provided in plural, and the plurality of focal points may be formed in a single scan line. A time delayed voltage pulse may be inputted as a transmission pulse to each of the transducer elements provided in the transducer 110.

When the transducer 10 receives echo ultrasound energy after completing irradiating diagnostic ultrasound energy, the echo delay unit 213 may receive a digital signal corresponding to echo ultrasound energy from the analog-digital converter 205, and may delay a time of a digital signal of each of the transducer elements provided in the transducer 110 based on a focal point and a steering angle of ultrasound against a target point.

For example, the echo delay unit 213 may flexibly set a delay frequency based on at least one parameter from among whether two dimensional transducer array 110 is included, a depth of focal point, a steering angle, a gauge size, and the number of activated transducer elements. The echo delay unit 213 may apply a delay time to the digital signal of each of the transducer elements provided in the transducer 110 according to a set delay frequency.

Meanwhile, FIG. 2 illustrates that a digital signal converted by the analog-digital converter 205 is inputted to the echo delay unit 213, but a sequence is not limited thereto. An analog signal delayed in the echo delay unit 213 may be inputted to the analog-digital converter 205.

The adder 214 may add a digital signal of each of the transducer elements provided in the transducer 110, in which a delay time is applied by the echo delay unit 213, to focus as a single digital signal. The focused digital signal may be outputted from the probe 100 to be transmitted to the signal processor 220 of the main body 200, and may be subjected to various image processing operations in order to generate ultrasound images by the image processor 230 after signal processing which is performed by the signal processor 220.

As illustrated in FIG. 2, the analog-digital converter 205 is placed inside the main body 200, but is not limited thereto. The analog-digital converter 205 may be placed inside the probe 100.

In the ultrasound imaging apparatus 10, the beamformer 210 may be provided in the main body 200 in correspondence to a back-end, as mentioned above or may be provided in the probe 100 in correspondence to a front-end. According to exemplary embodiments, all or some components of the beamformer 210 may be any placed in a front-end or a back-end.

The signal processor 220 may convert a focused digital signal received from the probe 100 into a signal which is in a proper form for image processing. For example, the signal processor 220 may perform filtering to remove a noise signal from outside of a desired frequency band.

The signal processor 220 may be realized by a Digital Signal Processor (DSP) and may generate ultrasound images by performing envelope detection processing configured to detect an echo ultrasound size based on a focused digital signal.

The image processor 230 may generate images based on ultrasound image data generated by the signal processor 220 so that a user, such as a doctor and a patient, may visually examine an object ob, such as the inside of the human body.

The image processor 230 may generate an internal diagnostic image which is usable to diagnose the inside of an object ob, a contrast agent image which is usable to detect the contrast agents 500 injected in an object ob, and a combined image of the internal diagnostic image and a contrast agent image according to a diagnostic mode.

The internal diagnostic mode may include at least one image from among an Amplitude mode (A-mode) image, a Brightness mode (B-mode) image, a Doppler mode (D-mode) image, an Elastography mode (E-mode) image, a Motion mode (M-mode) image.

The contrast agent image may be a Cadence Pulse Sequencing mode (CPS-mode) image.

The combined image may include an image that combines at least one image of an A-mode image, a B-mode image, a D-mode image, a E-mode image, and a M-mode image, and a CPS-mode image.

Hereinafter a B-mode image will be described as an example of an internal diagnostic image, a CPS-mode image will be described as an example of a contrast agent image, and an image that combines a B-mode image and a CPS-mode image will be described as an example of a combined image.

Figure 8:
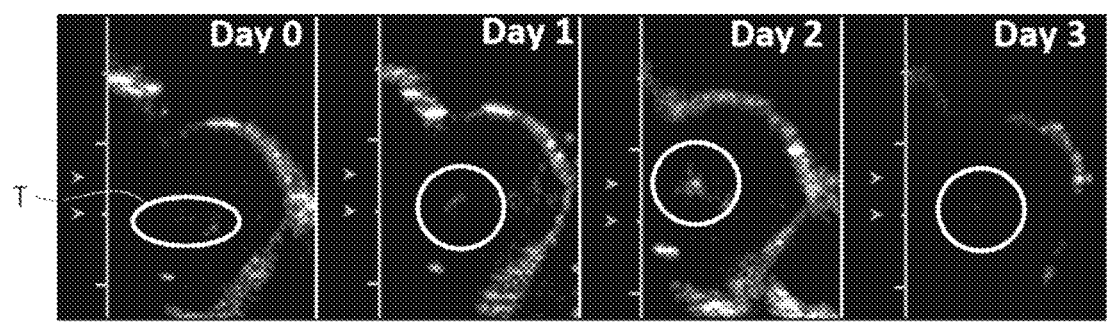
FIG. 8 is a view illustrating a cadence pulse sequencing mode (CPS-mode) image generated by an imaging processor.

FIG. 7 is a view illustrating a B-mode image generated by an imaging processor, FIG. 8 is a view illustrating a CPS-mode image generated by an imaging processor, FIGS. 9A, 9B, 9C, 9O, 10, 11, and 12 are views illustrating combined images of the B-mode image and the CPS-mode image generated by an imaging processor, and FIG. 13 is a view illustrating a process of generating a combined image based on an area selected by a user.

According to an exemplary embodiment, the image processor 230 may generate a B-mode image so that a size of echo ultrasound reflected from an object ob, in which diagnostic ultrasound is irradiated, is converted into a brightness and displayed on an image, as illustrated in FIG. 7.

A user may confirm overall internal tissues of the object ob by using a B-mode image displayed on the display unit 300. In this aspect, the user may confirm information about surrounding tissues as well as a target tissue by using the B-mode image.

According to an exemplary embodiment, the image processor 230 may detect echo ultrasound energy having strong energy intensity to detect the contrast agents 500 injected into a target tissue, and may generate a CPS-mode image so that an energy intensity of the contrast agents 500 may be converted into a brightness and displayed on the display unit 300, as illustrated in FIG. 8.

Referring to FIG. 8, when the contrast agents 500 including the shell 510 composed of a silica nanostructure, and the core 520 composed of perfluorocarbon are injected into blood vessels of an object ob, and when high intensity focused ultrasound energy is irradiated to a target tissue T, the contrast agents 500 may be activated in the target tissue T (Day 0).

According to the activation of the contrast agents 500, bubbles of gas perfluorocarbon may reflect diagnostic ultrasound energy and generate echo ultrasound energy. In this case, the image processor 230 may generate a CPS mode image so that the contrast agents 500 having strong brightness, which corresponds to strong echo ultrasound energy, may be displayed on the target tissue T (Day 2, Day 3).

As time passes, the contrast agents 500 may be dissolved or discharged from the object ob. In this case, the image processor 230 may generate a CPS-mode image so that a target tissue T may be displayed to be dark (Day 4).

In addition, the image processor 230 may improve a contrast of the CPS-mode image so that the target tissue T, in which the contrast agents 500 is injected, may be displayed to be brighter than the surrounding tissues.

Meanwhile, an echo ultrasound intensity may be displayed in a brightness in a CPS mode image of FIG. 8, but is not limited thereto. An echo ultrasound intensity may be displayed in a color, or in any of various ways in a CPS mode image.

A user may confirm a location and a size of a target tissue by using a CPS-mode image displayed on the display unit 300.

Figure 9A:
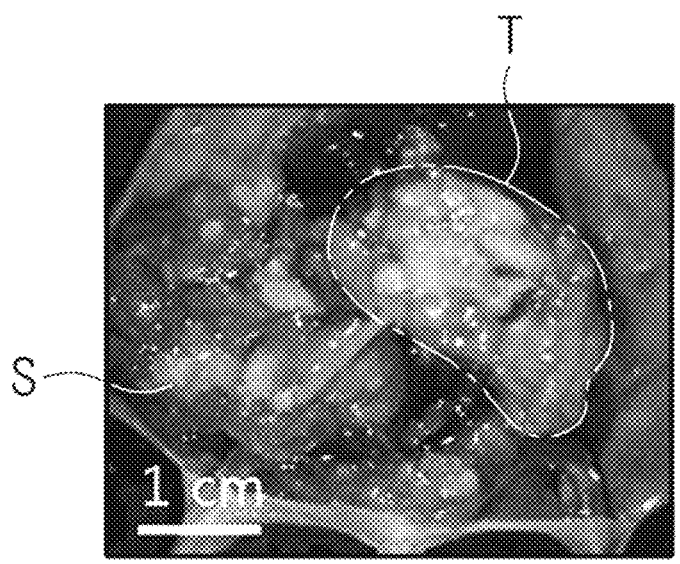
FIGS. 9A, 9B, 9C, 9D, 10, 11, and 12 are views illustrating combined images of the B-mode image and the CPS-mode image generated by an imaging processor.
Figure 9B:
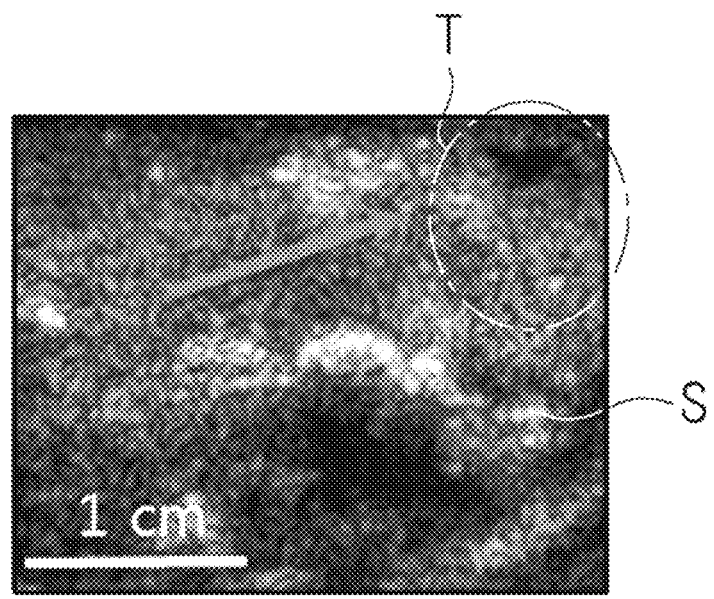
Figure 9C:
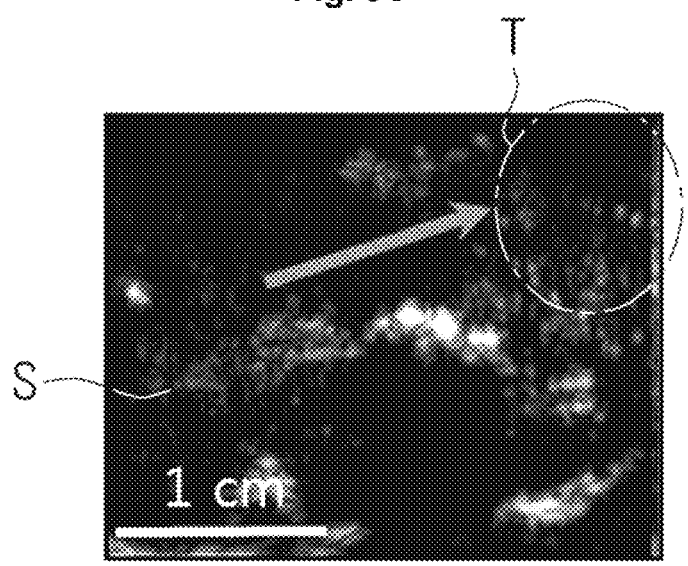
Figure 9D:
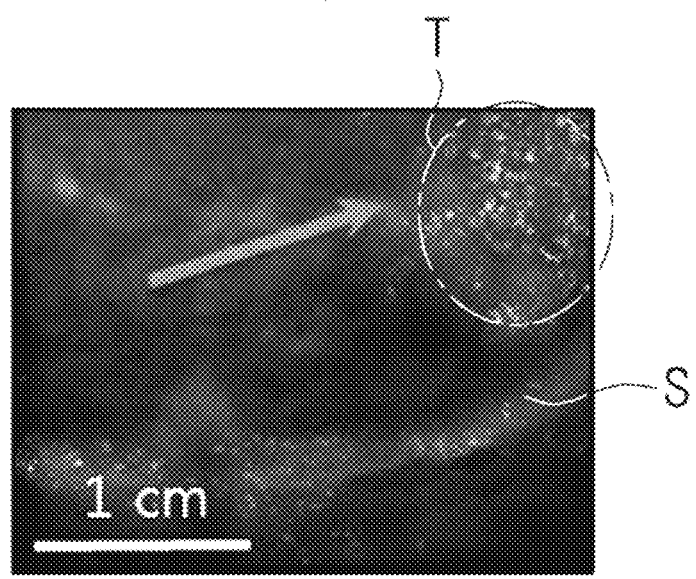

According to an exemplary embodiment, the image processor 230 may generate a combined image (as shown in FIG. 9D) that combines a B-mode image (i.e., FIG. 9B) and a CPS-mode image (i.e., FIG. 9C), as illustrated in FIGS. 9A, 9B, 9C, and 9D.

In a case a tissue of an object ob is present, as illustrated in FIG. 9A, and when irradiating diagnostic ultrasound energy to the object, the image processor 230 may generate a B-mode image of FIG. 9B based on echo ultrasound energy.

In addition, when the contrast agents 500 are injected into an object ob and high intensity focused ultrasound energy and diagnostic ultrasound energy are irradiated to the object ob, the image processor 230 may generate a CPS-mode image of FIG. 9C based on echo ultrasound energy. The CPS-mode image may display the contrast agent 500 selectively stacked on a target tissue to be bright, as illustrated in FIG. 9C.

In addition, the image processor 230 may generate a combined image that combines a B-mode image and a CPS-mode image, as illustrated in FIG. 9D.

Figure 10:
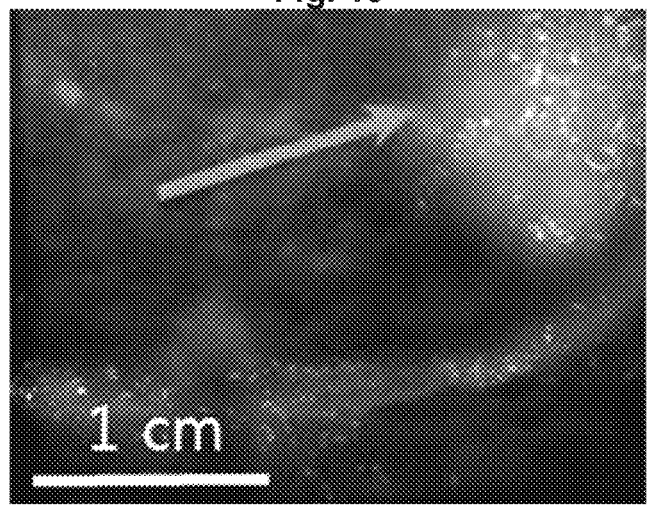

In this case, the image processor 230 may extract a pixel having a brightness that is greater than a predetermined threshold from a CPS-mode image, as illustrated in FIG. 10, and may combine the extracted pixel with a B-mode image.

Figure 11:
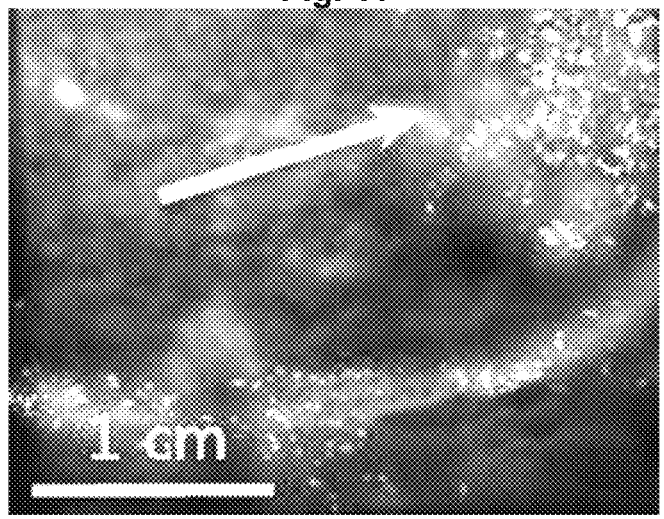

As illustrated in FIG. 11, the image processing unit 230 may combine a CPS-mode image having improved a contrast, a brightness, or a sharpness, and a B-mode image having reduced a contrast, a brightness, or a sharpness. Accordingly, the contrast agents 500 injected into a target tissue T may be displayed more clearly and the surrounding tissue S may be displayed smoothly.

Figure 12:
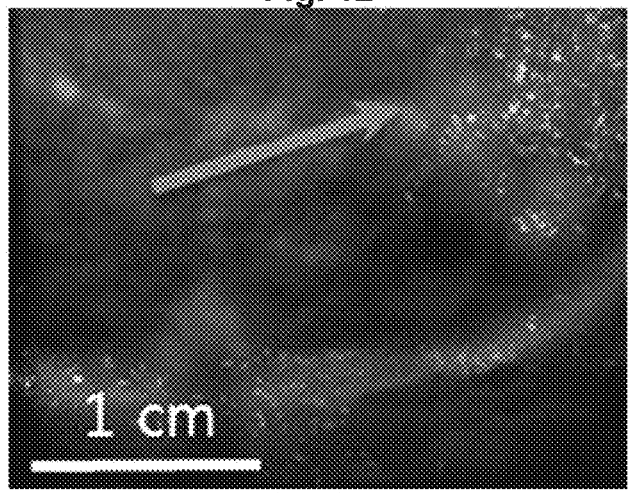

As illustrated in FIG. 12, the image processing unit 230 may combine a CPS-mode image in which echo ultrasound energy intensity of a target tissue T is displayed in color, and a B-mode image having reduced a contrast, a brightness, or a sharpness. Accordingly, a user may confirm a degree of distribution of the contrast agents 500 injected into a target tissue T.

Figure 13A:
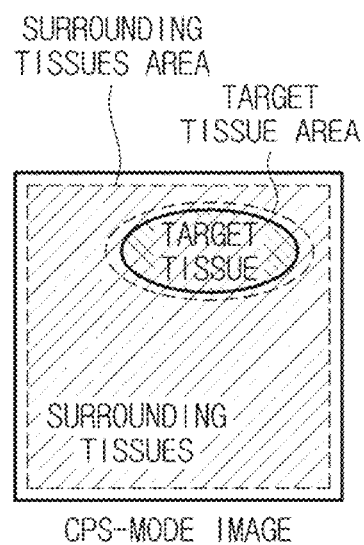
FIGS. 13A, 13B, and 13C are views illustrating a process of generating a combined image based on an area selected by a user.
Figure 13B:
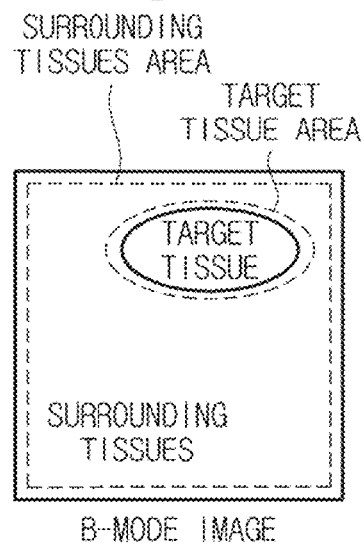
Figure 13C:
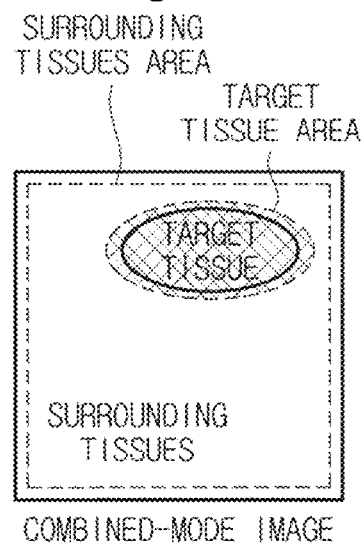

As illustrated in FIGS. 13A, 13B, and 13C, the image processing unit 230 may extract a target tissue area, which is selected by a user, from a CPS mode image (as illustrated in FIG. 13A), may extract a rest area excepting the target tissue area (hereinafter referred to as surrounding tissues) from a B-mode image (i.e., FIG. 13B), and may generate a combined image (i.e., FIG. 13C). In addition, the image processor 230 may overlap a target tissue area, which is extracted from the CPS-mode image to generate a combined image, on the B-mode image.

Alternatively, the image processor 230 may generate a combined image by combining a CPS-mode image, in which a volume rendering is performed on a target tissue T, and an internal diagnostic image in which the inside (a target tissue area and a surrounding area are included) of an object ob is displayed smoothly. The volume rendering may represent an image processing to generate a three dimensional (3D) image by adding a reality to a two dimensional (2D) image by using a shadow, a color, a contrast, etc.

Figure 14:
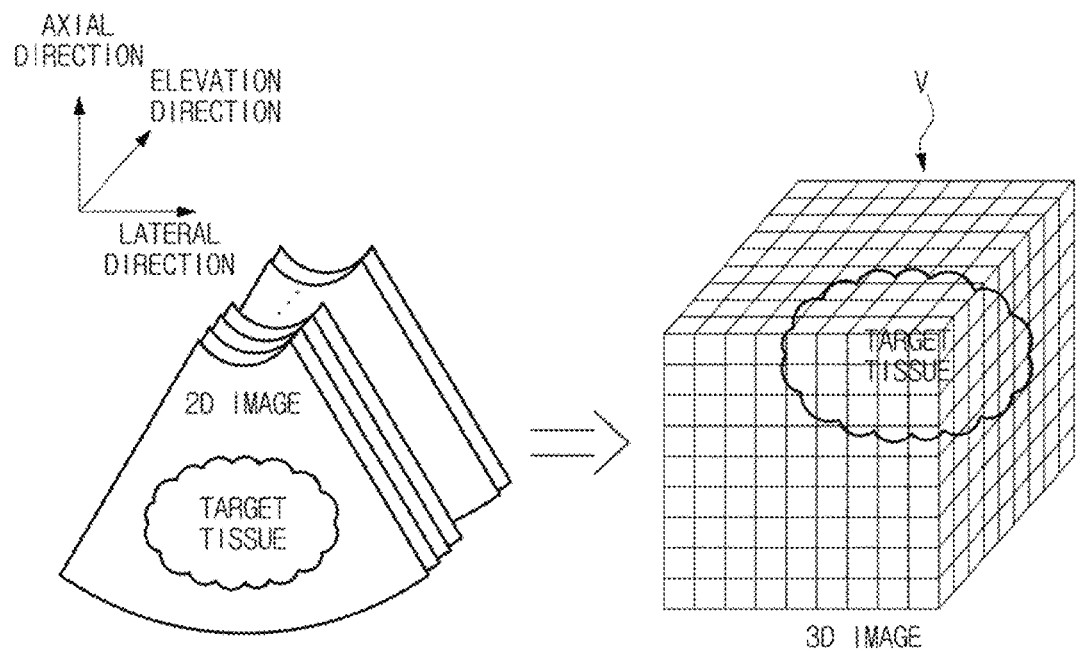
FIG. 14 is a view illustrating a process of generating a combined image by performing volume rendering to an image of a target tissue.

FIG. 14 is a view illustrating a process of generating a combined image by performing volume rendering to an image of a target tissue.

As illustrated in a left side of FIG. 14, the image processor 230 may generate a 2D image of a tissue of an object ob. The 2D image may be defined by an axial direction and a lateral direction. The image processor 230 may generate a plurality of 2D images by using a received signal acquired in an elevation direction by mechanical steering by using a one dimensional array probe 100 or electrical steering by using a two dimensional array probe 100. The image processor 230 may generate a 3D image (V) by stacking a plurality of 2D images, as illustrated in a right side of FIG. 14.

In particular, the image processor 230 may generate a 3D CPS-mode image of a target tissue in order to provide information about a thickness and a depth of a tissue to a user. For example, the probe 100 may employ any of a 3D probe 100, a matrix ultrasonic probe 100, a mechanical probe 100 or the like.

The image processor 230 may perform volume rendering on the target tissue area included in the combined image after generating the combined image.

The image processor 230 may transmit an ultrasound image generated by using ultrasound image data to the display unit 300.

Referring to FIG. 2 again, the control unit 240 may control overall operation of the ultrasound imaging apparatus 10. Particularly, the control unit 240 may generate control signals to control at least one of the analog-digital converter 205, the beamformer 210, the image processor 230, the storage unit 250, the probe 100, and the display unit 300 in response to instructions or commands of programs stored in the storage unit 250 or input via the input unit 400.

In particular, the control unit 240 may control the probe 100 so that the probe 100 may irradiate high intensity focused ultrasound energy or diagnostic ultrasound energy to an object ob, and the control unit 240 may control the probe 100 so that the probe 100 may receive echo ultrasound energy.

In addition, the control unit 240 may control the beamformer 210 so that the beamformer 210 may generate pulses, apply a time to pulses, apply a delay time to a received signal from the transducer 110, and/or add a signal to respond to instructions or commands of programs stored in the storage unit 250 or input via the input unit 400. A detailed description of the beamformer 210 is provided above, and thus will be omitted below.

The control unit 240 may control the image processor 230 so that the image processor 230 may generate an ultrasound image and perform an image processing operation in response to instructions or commands of programs stored in the storage unit 250 or input via the input unit 400.

The control unit 240 may control the storage unit 250 so that the storage unit 250 may store an ultrasound image and load an ultrasound image in response to instructions or commands of programs stored in the storage unit 250 or input via the input unit 400.

The control unit 240 may control the display unit 400 so that the display unit may display an ultrasound image in response to instructions or commands of programs stored in the storage unit 250 or input via the input unit 400.

The control unit 240 may include a processor, a read-only memory (ROM) in which control programs for control of the ultrasound imaging apparatus 10 are stored, and a random access memory (RAM) in which signals or data inputted from the outside are stored or which is used as a storage area to correspond to various operations performed in the ultrasound imaging apparatus 10.

The processor may be realized in a shape of System on Chip (SoC) which includes a core and a graphics processing unit (GPU). The processor may include any of a single core, a dual core, a triple core, a quad core and various multiple cores.

The control unit 240 may include a graphic processing board which is a separated circuit board, which is electrically connected, includes a processor, and RAM or ROM. The process, a ROM, and RAM may be connected to each other via an internal bus.

As mentioned above, the RAM and the ROM may be a component provided in the control unit 240, or may be a component provided in a separate storage unit.

The storage unit 250 may be configured to store programs and data related to the ultrasound imaging apparatus 10, and may include a program portion and a data portion. The program portion may store programs that relate to functions of the ultrasound imaging apparatus 10, and the data portion may store data generated according to an operation of the ultrasound imaging apparatus 10, or predetermined data. Data stored in the storage unit 250 may be displayed for a user via the display unit 300.

The storage unit 250 may employ nonvolatile memory, such as, any of Read Only Memory (ROM), Random Access Memory (RAM), Programmable Read Only Memory (PROM), Erasable Programmable Read Only Memory (EPROM), and Flash memory, or volatile memory, such as Random Access Memory (RAM), or Hard Disk Drive (HDD), or CD-ROM, but is not limited thereto. The storage unit 250 may be realized in any of various shapes which are well known to persons of ordinary skill in the art.

The display unit 300 may display an ultrasound image generated by the image processor 230 to a user.

Figure 15:
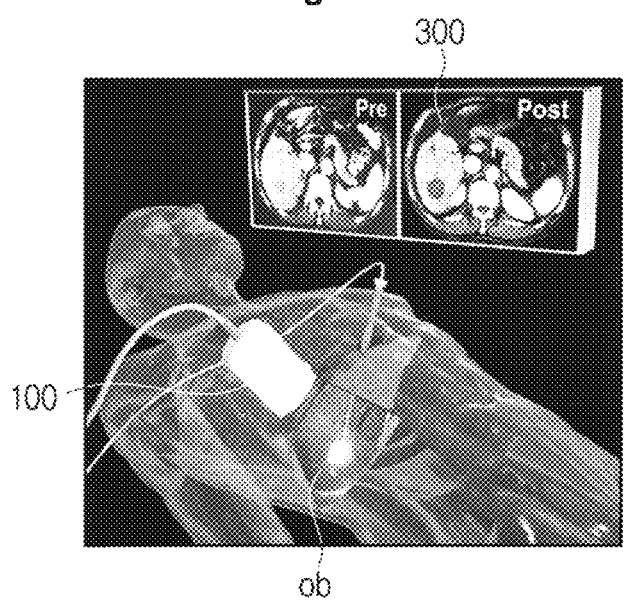
FIG. 15 is a view illustrating a condition in which a display unit is used.
Figure 16:
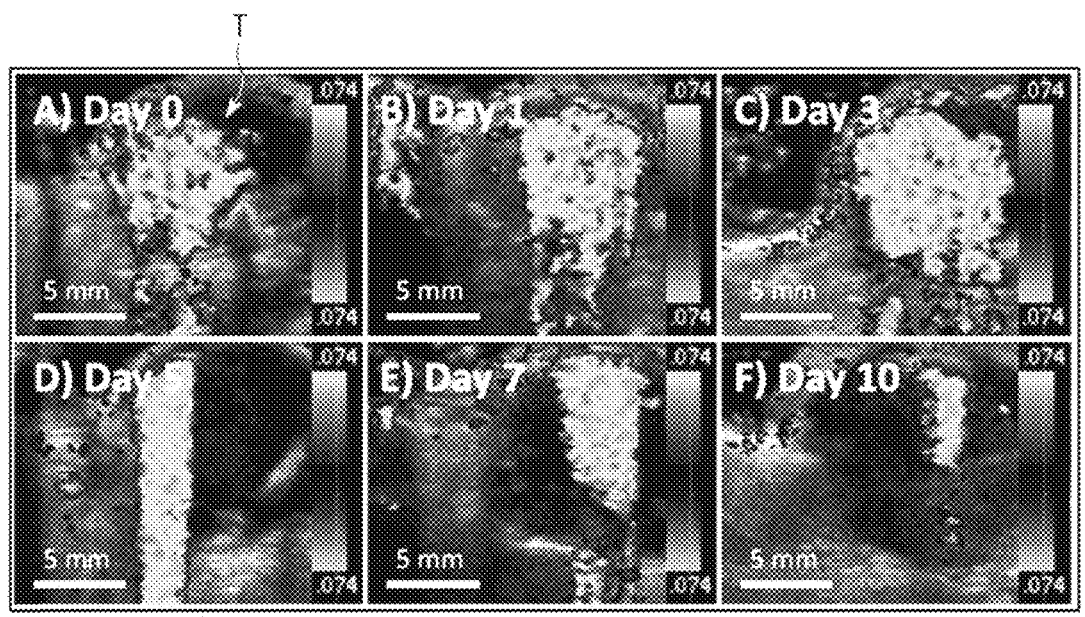
FIG. 16 is a view illustrating a combined image displayed by a display unit.

FIG. 15 is a view illustrating a condition in which a display unit is used, and FIG. 16 is a view illustrating a combined image as displayed by a display unit.

In particular, according to an exemplary embodiment, the display unit 300 may display a combined image to a user wherein the combined image is combined a B-mode image and a CPS mode image, both of which are generated by the image processor 230.

At least one of a B-mode image, a CPS-mode image and a combined image may be generated in a 2D image and a 3D image.

As illustrated in FIG. 15, when the combined image is displayed to a user, the display unit 300 may guide a target tissue location while providing the combined image to the user. The user may place an ultrasound focal point at a guided target tissue location and irradiate medical ultrasound energy through the probe 100. The medical ultrasound energy may include high intensity focused ultrasound energy.

In addition to guiding a target tissue location to a user, the display unit 300 may display an amount of change of the contrast agents 500 injected into a target tissue as time passes.

FIG. 16 illustrates an example of a screen of the display unit 300 which changes as time passes.

Referring to FIG. 16, when the image processor 230 performs volume rendering on a target tissue T, the contrast agents 500, which exist in the target tissue on a B-mode image of a tissue in an object, may be displayed on a 3D CPS-mode image having a color and a contrast.

While displaying an amount of change of the contrast agents 500 in time series, the display unit 300 may further display an elapsed time (Day 1 to Day 10) after the contrast agents 500 are injected, an injection interval of the contrast agents 500, or a time of injection request of the contrast agents 500.

Meanwhile, a combined image displayed on the display unit 300 may be an image in which volume rendering is performed or various image processing is performed by the image processor 230.

In addition, the display unit 300 may display a target tissue by using a marker. The marker may include a color and an arrow indicating the target tissue.

In addition, the display unit 300 may further display diagnostic information that relates to a target tissue, such as the presence of an abnormality, and may display a degree of abnormality in various colors, but is not limited thereto.

The display unit 300 may employ any of a plasma display panel (PDP), a light emitting diode (LED) or a liquid crystal display (LCD). In addition, the display unit 300 may employ a 3D display unit which is capable of displaying 3D images. The display unit 300 may include a touch screen. When the display unit 300 includes a touch screen, the display 300 may perform a function of the input unit 400.

The touchscreen may employ a resistive touchscreen panel or a capacitive touchscreen panel. Alternatively, the touch screen may be realized by a touch screen panel by using ultrasound or infrared light.

The display unit 300 may display images according to a diagnostic mode selected by a user. When a user does not select a mode, the display unit 300 may display images in a predetermined default mode (e. g., B-mode).

Referring to FIG. 2 again, the input unit 400 may enable a user to input control commands of the ultrasound imaging apparatus 10, and may be provided with a plurality of screens so that a user may input control commands while watching the display unit 300 displaying various images. A user may select a diagnostic mode, set an object and a target tissue to be detected, and/or select an image to be displayed on the display unit 300, via the input unit 400.

In particular, a user may select one mode from among a Amplitude mode (A-mode), a Brightness mode (B-mode), a Doppler mode (D-mode), a Elastography mode (E-mode), a Motion mode (M-mode), and a cadence pulse sequencing mode (CPS-mode) via the input unit 400, and may further select a combined mode in order to generate a combined image via the input unit 400.

For example, when a user selects a B-mode via the input unit 400, a B-mode image of an object may be generated, and when a user selects a CPS-mode via the input unit 400, a CPS-mode image of an object may be generated. In addition, when a combined mode is selected via the input unit 400, a B-mode image and a CPS-mode image may be generated and then a combined image may be generated based on the B-mode image and the CPS-mode image.

The input unit 400 may include at least one from among a keyboard, a mouse, a trackball, a touch screen, a foot switch, or a foot pedal, but is not limited thereto.

The input unit 400 may be provided on an upper portion of the main body 200 as shown in FIG. 1, or may be provided on a lower portion of the main body 200 when the input unit 400 is implemented with a foot switch or a foot pedal.

When the input unit 400 is implemented in a Graphical User Interface (GUI), i.e., in software similarly as a touch screen, the input unit 400 may be displayed on the display unit 300, which will be described later.

One or more probe holders may be provided on or around the input unit 400 to hold the probe 100. Therefore, a user may keep the probe 100 in the probe holder while the ultrasound imaging apparatus 10 is not used.

In the main body 200, at least one female connector may be provided, and the female connector may be coupled to the male connector which is connected to a cable of the probe 100. Accordingly, a signal generated by the main body 200 and a signal generated by the probe may be transmitted and received. For example, a transmission signal generated by the main body 200 may be transmitted to the transducer 110 via the male connector connected to the female connector of the main body 200, and a cable.

In a lower portion of the main body 200, a plurality of casters may be mounted to be fixed on a certain place or moved in a certain direction.

According to exemplary embodiments, some components provided in the ultrasound imaging apparatus 100 may be implemented as modules. Here, the term "module" may represent a software element or a hardware element, such as a Field Programmable Gate Array (FPGA) or an Application Specific Integrated Circuit (ASIC), and the module may perform a predetermined role. However, the module is not limited to software or hardware. Further, the module may be constructed to exist in an addressable storage module, or to play one or more processors.

The module may include elements (e.g., software elements, object-oriented software elements, class elements and task elements), processors, functions, properties, procedures, subroutines, segments of a program code, drivers, firmware, a microcode, a circuit, data, a database, data structures, tables, arrays, and variables. Herein, functions provided by components and modules may be provided by a smaller number of combined larger components and modules, or by a larger number of divided smaller components and modules. In addition, the components and modules may be realized to operate one or more CPUs in a device.

Figure 17:
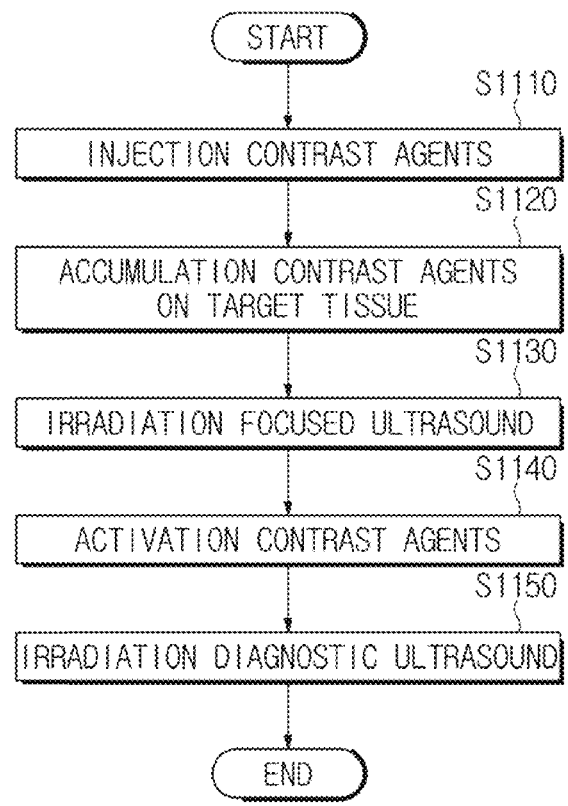
FIG. 17 is a flow chart illustrating a control method of an ultrasound imaging apparatus, in accordance with an exemplary embodiment, when irradiating ultrasound to an object.

With reference to FIGS. 17, 18, 19, and 20, a control method of the ultrasound imaging apparatus 10 will be described. FIG. 17 is a flow chart illustrating a control method of an ultrasound imaging apparatus, in accordance with an exemplary embodiment, when irradiating ultrasound to an object.

Referring to FIG. 17, in operation S1110, contrast agents may be injected into an object via blood vessels of the object, such as a vein. The contrast agents may include a shell composed of a silica nanostructure, and a core composed of a liquid perfluorocarbon or a gas perfluorocarbon.

In this case, the shell composed of a silica nanostructure may have a diameter of greater than 10 nm and less than 3000 nm that is smaller than blood vessels around a tumor and larger than normal blood vessels.

The shell composed of a silica nanostructure may permeate a tumor through blood vessels around the tumor that is looser than normal blood vessels so that the contrast agents may be selectively stored on a target tissue, such as a tumor and a cancer, in operation S1120.

In this case, an ultrasound imaging apparatus may generate a CPS-mode image of a target tissue and may display the image to a user so that the user may conform that the contrast agents may be stacked on the target tissue.

In operation S1130, the ultrasound imaging apparatus may irradiate focused ultrasound energy to a target point so that the contrast agents stacked on the target tissue may be activated.

In comparison with diagnostic ultrasound energy, the focused ultrasound energy may include a single pulse having a short time to be applied and being applied by being focused at a target point.

Among focused ultrasound energy applications, focused ultrasound energy which generates an energy intensity of greater than 3 MPa at a target point may be referred to as high intensity focused ultrasound energy, and hereinafter high intensity focused ultrasound energy will be described as an example of focused ultrasound energy.

When a silica nanostructure in the contrast agents, which is stacked on the target tissue, is be dissolved by focused ultrasound energy and liquid perfluorocarbon is be evaporated, the contrast agents may be activated in operation S1140.

When the contrast agents are activated, in operation S1150, the ultrasound imaging apparatus may irradiate diagnostic ultrasound energy to an object in order to generate an ultrasound image.

The diagnostic ultrasound energy may represent ultrasound energy irradiated from the probe in order to generate diagnostic images used to examine or diagnose the inside of an object or to generate a contrast agent image used to detect the contrast agents injected into a target tissue.

The diagnostic ultrasound energy applications may have different frequency bands or energy intensities with respect to each other according to the diagnostic mode.

The diagnostic mode may be any of an Amplitude mode (A-mode), a Brightness mode (B-mode), a Doppler mode (D-mode), an Elastography mode (E-mode), a Motion mode (M-mode), and a cadence pulse sequencing mode (CPS-mode), but is not limited thereto. The diagnostic mode may include a combined mode.

As illustrated in FIG. 17, in operation S1150, the diagnostic ultrasound energy is irradiated after the contrast agents are activated, but is not limited thereto. Alternatively, the ultrasound imaging apparatus may irradiate the diagnostic ultrasound energy to the object when injecting the contrast agent in operation S1110, and thus an ultrasound image may be continuously or intermittently provided to a user.

Figure 18:
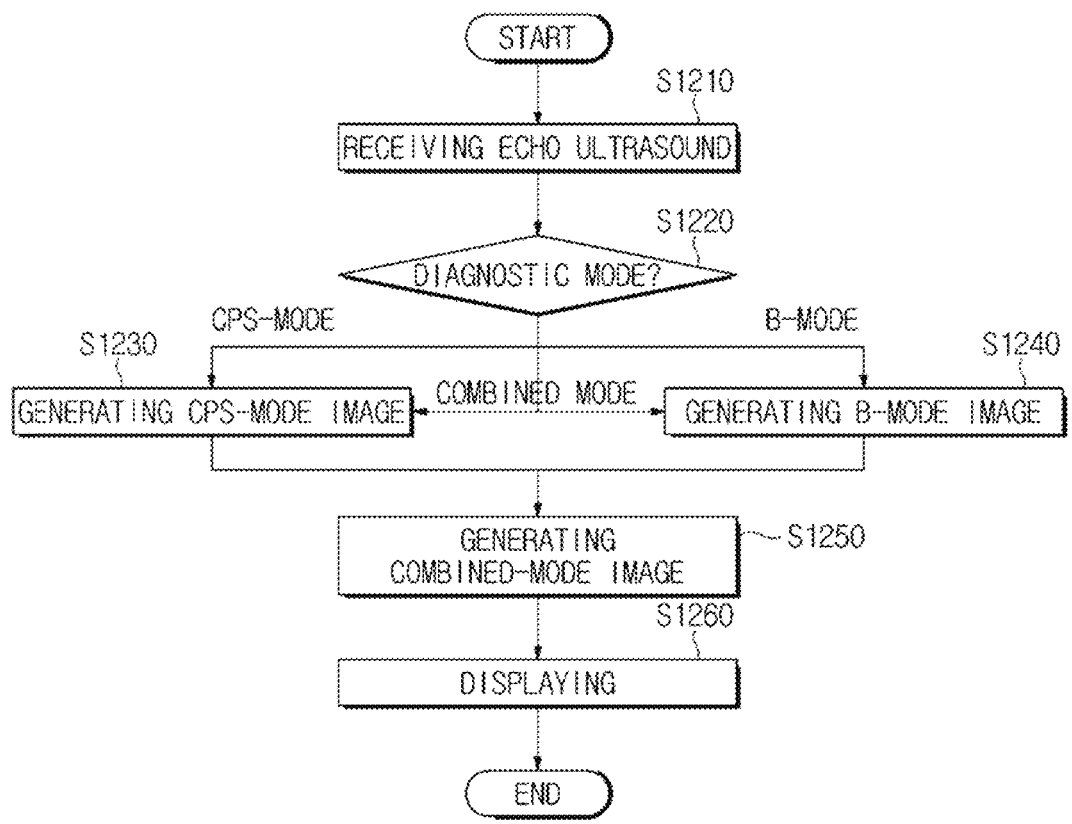
FIG. 18 is a flow chart illustrating a control method of an ultrasound imaging apparatus, according to an exemplary embodiment, when receiving echo ultrasound reflected from an object.

FIG. 18 is a flow chart illustrating a control method of an ultrasound imaging apparatus, according to an exemplary embodiment, when receiving echo ultrasound energy reflected from an object.

In operation S1210, an ultrasound imaging apparatus may receive echo ultrasound energy reflected from an object.

The echo ultrasound energy may include ultrasound energy reflected from the object into which ultrasound energy is irradiated, and may have any of various frequency bands and energy intensities in order to generate various ultrasound images according to a diagnostic mode.

The ultrasound imaging apparatus may receive a diagnostic mode from a user in operation S1220, and may generate a contrast agent image and an internal diagnostic image according to the received diagnostic mode in respective operations S1230 and S1240.

For example, when receiving a B-mode as a diagnostic mode from a user, the ultrasound imaging apparatus according to an exemplary embodiment may generate a B-mode image as an internal diagnostic image in operation S1240, and when receiving a CPS-mode as a diagnostic mode from a user, the ultrasound imaging apparatus may generate a CPS mode image as a contrast agent image in operation S1230.

When receiving a combined mode as a diagnostic mode from a user, the ultrasound imaging apparatus according to another exemplary embodiment may generate a B-mode image as an internal diagnostic image and a CPS mode image as a contrast agent image in respective operations S1240 and S1230.

The ultrasound imaging apparatus may generate a combined image by combining an internal diagnostic image with a contrast agent image in operation S1250.

For example, the ultrasound imaging apparatus may generate a combined image by combining a B-mode image with a CPS-mode image.

In this case, the ultrasound imaging apparatus may perform a predetermined image processing operation with respect to an internal diagnostic image and a contrast agent image, which will be described below with reference to FIG. 19.

The ultrasound imaging apparatus may display a combined image to a user via the display unit in operation S1260.

For example, the ultrasound imaging apparatus may display only a combined image or all of an internal diagnostic image, a contrast agent image and a combined image on a screen of the display unit.

In addition, the ultrasound imaging apparatus may selectively display one or more images from among an internal diagnostic image, a contrast agent image and a combined image on a screen of the display unit according to a manipulation of a user.

The ultrasound imaging apparatus may further output a screen to provide any of a procedure guide, diagnosis data, etc. to a user, which will be described below with reference to FIG. 20.

Hereinafter an image processing operation, which is performed when the ultrasound imaging apparatus generates a combined image in operation S1250, will be described.

Figure 19:
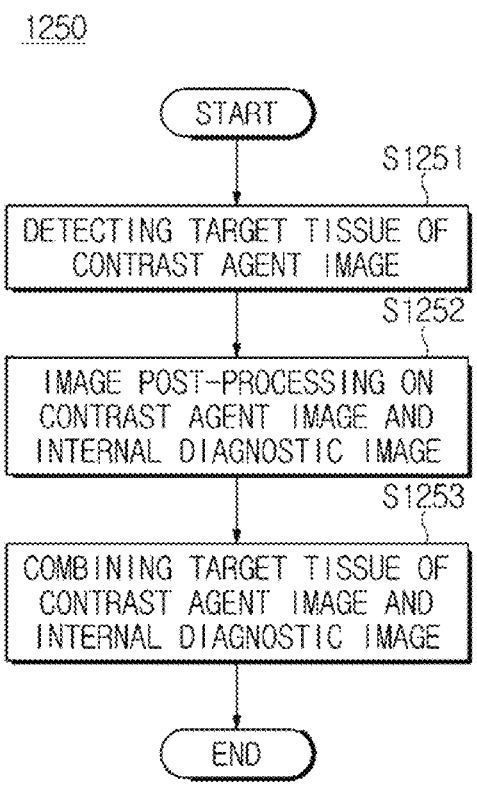
FIG. 19 is a flow chart illustrating a method for generating a combined image, according to an exemplary embodiment.

FIG. 19 is a flow chart illustrating a method for generating a combined image, according to an exemplary embodiment.

For example, in operation S1251, the ultrasound imaging apparatus may extract a target tissue from a contrast agent image. In this case, the ultrasound imaging apparatus may extract a remainder area excepting a target tissue area (that is, a surrounding tissue area) from an internal diagnostic image as a surrounding tissue.

For example, the ultrasound imaging apparatus may extract a target tissue area from a contrast agent image by setting a selected area as a target tissue area according to a manipulation of a user.

In addition, the ultrasound imaging apparatus may extract a pixel which has a brightness that is greater than a predetermined threshold as a target tissue from a contrast agent image.

In operation S1252, the ultrasound imaging apparatus may perform an image post-processing operation with respect to a contrast agent image and an internal diagnostic image.

For example, the ultrasound imaging apparatus may improve a contrast, a brightness, and/or a sharpness of a contrast agent image, and may reduce a contrast, a brightness, and/or a sharpness of an internal diagnostic image. In this case, the ultrasound imaging apparatus may improve a contrast, a brightness, and/or a sharpness of a detected target tissue of a contrast agent image, and may reduce a contrast, a brightness, and/or a sharpness of surrounding tissues of an internal diagnostic image.

The ultrasound imaging apparatus may perform a volume rendering operation with respect to a detected target tissue image in a contrast agent image, and thus may generate a 3D image of a target tissue.

Due to an image post-processing operation of the ultrasound imaging apparatus, the contrast agents injected into a target tissue may be displayed more clearly and surrounding tissues may be displayed smoothly.

In operation S1253, the ultrasound imaging apparatus may combine a target tissue image of a contrast agent image in which an imaging post-processing operation is performed with an internal diagnostic image in which an imaging post-processing operation is performed. When surrounding tissues are detected from an internal diagnostic image, the ultrasound imaging apparatus may combine a target tissue image of the contrast agent image with a surrounding tissues image of an internal diagnostic image.

According to another exemplary embodiment, the ultrasound imaging apparatus may provide any of a procedure guide, diagnosis data, etc. to a user, when displaying a combined image.

Figure 20:
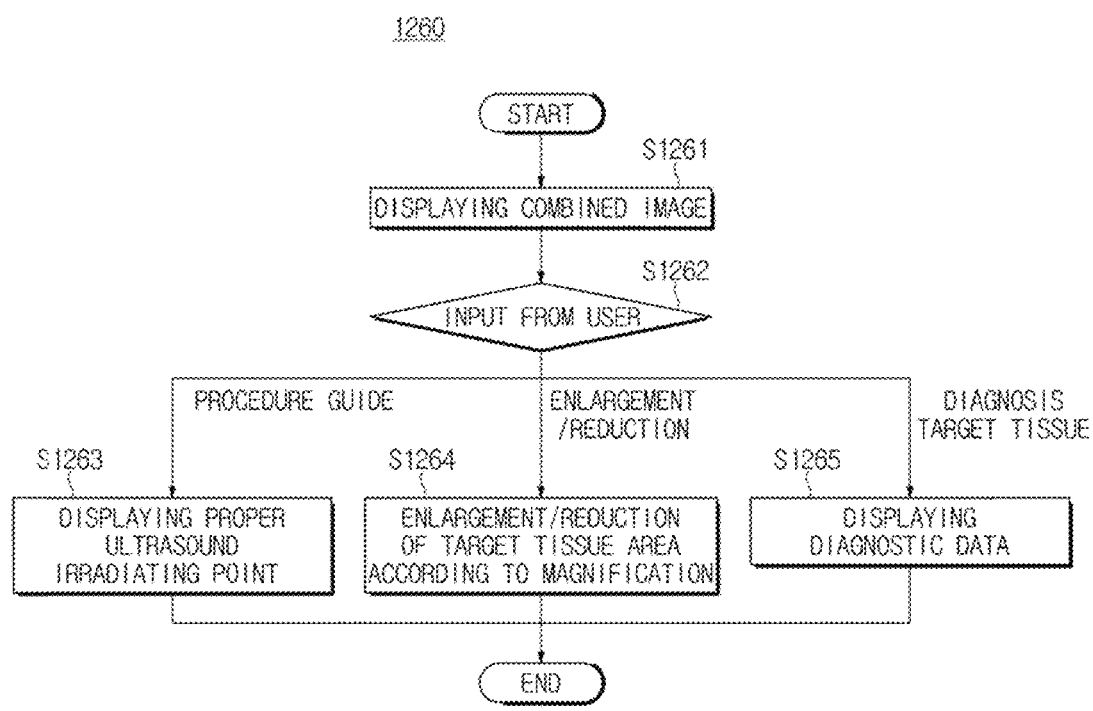
FIG. 20 is a flow chart illustrating a control method of an ultrasound imaging apparatus, in accordance with another exemplary embodiment.

FIG. 20 is a flow chart illustrating a control method of an ultrasound imaging apparatus, in accordance with another exemplary embodiment.

When a combined image is displayed in operation S1261, the ultrasound imaging apparatus may receive a command according to a manipulation of a user via the input unit in operation S1262.

For example, when a user inputs a mode to be supplied with a procedure guide from the ultrasound imaging apparatus, the ultrasound imaging apparatus may display a proper position for irradiating ultrasound energy via the display unit in operation S1263.

For example, the proper position for irradiating ultrasound energy may be a position in which a target tissue detected by the ultrasound imaging apparatus may be placed.

When a user inputs a command of enlarging or a command of reducing of a combined image, the ultrasound imaging apparatus may enlarge or reduce a detected target tissue area according to an inputted magnification or a predetermined magnification on a screen of the display unit in operation S1264.

When a user inputs a command of diagnosing a target tissue, in operation S1265, the ultrasound imaging apparatus may display any of various data related to a target tissue, such as a size of a target tissue, a density of a target tissue and whether a target tissue is normal, as diagnostic data via the display unit.

The ultrasound imaging apparatus 100 and the control method thereof may be implemented as a computer code on a transitory or non-transitory computer readable recording medium. The computer readable recording medium may include any of various kinds of recording medium stored data decrypted by the computer system. For example, there may be a Read Only Memory (ROM), a Random Access Memory (RAM), a magnetic tape, a magnetic disk, a flash memory, and an optical data storage device. In addition, the medium may be distributed to computer systems over a network, in which computer-readable code may be stored and executed in a distributed manner.

As is apparent from the above description, according to the proposed ultrasound imaging apparatus and a control method thereof, a contrast agent image displaying contrast agents stacked on a target tissue may be generated, and a combined image that combines the contrast agent image and an internal diagnostic image. Accordingly, a user may correctly confirm a position of a target tissue in comparison with an internal diagnostic image of an object.

According to the proposed probe, by irradiating focused ultrasound energy, contrast agents may be activated by using a relatively small amount of energy, and echo ultrasound energy may be received and used to generate a combined image of a contrast agent image and an internal diagnostic image.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. An ultrasound imaging apparatus comprising:
a controller configured to generate a control signal to control an operation of a probe;
a transceiver configured to transmit the control signal to the probe and to receive a signal transmitted from the probe; and
an image processor configured to generate at least one ultrasound image;
wherein the controller is further configured to control the operation of the probe so that the probe irradiates focused ultrasound energy when contrast agents composed of a silica nanostructure are injected into an object, and the controller is further configured to control the operation of the probe so that the probe irradiates diagnostic ultrasound energy when the focused ultrasound energy is irradiated,
wherein the controller is further configured to control the operation of the probe so that echo ultrasound energy reflected from the object is received when the diagnostic ultrasound energy is irradiated,
wherein the image processor is configured to generate the at least one ultrasound image based on an electrical signal when the transceiver receives the electrical signal corresponding to the echo ultrasound energy,
wherein the image processor is configured to generate a Cadence Pulse Sequencing mode (CPS-mode) image as a contrast agent image and a Brightness mode (B-mode) image as an internal diagnostic image, based on an electrical signal when the transceiver receives the electrical signal corresponding to the echo ultrasound energy,
wherein the image processor is configured to extract pixels having a brightness more than a predetermined threshold from the CPS-mode image and combine the extracted pixels with the B-mode image to form a combined image.

2. The ultrasound imaging apparatus of claim 1, wherein the controller is further configured to control the operation of the probe so that high intensity focused ultrasound (HIFU) energy is irradiated as the focused ultrasound energy.

3. The ultrasound imaging apparatus claim 1, further comprising:
a display configured to display the combined image.

4. The ultrasound imaging apparatus of claim 3, further comprising an input device configured to receive a magnification of the combined image from a user,
wherein the display is further configured to display a target point that is enlarged or reduced according to the received magnification.

5. The ultrasound imaging apparatus of claim 1, wherein the image processor is further configured to extract a target tissue from the contrast agent image and to combine the target tissue with the internal diagnostic image.

6. The ultrasound imaging apparatus of claim 5, wherein the image processor is further configured to generate a volume rendering image of the target tissue.

7. The ultrasound imaging apparatus of claim 5, further comprising a display configured to display diagnosis data related to the target tissue.

8. The ultrasound imaging apparatus of claim 1, wherein the image processor is further configured to detect a target tissue from the contrast agent image and to detect at least one surrounding tissue from the internal diagnostic image, and to combine a contrast agent image of the target tissue with an internal diagnostic image of the at least one surrounding tissue.

9. The ultrasound imaging apparatus of claim 1, wherein the image processor is further configured to perform an image post-processing operation with respect to the contrast agent image and the internal diagnostic image.

10. The ultrasound imaging apparatus of claim 9, wherein the image post-processing operation includes correcting or readjusting at least one from among a contrast, a brightness and a sharpness in each of the contrast agent image and the internal diagnostic image.

11. The ultrasound imaging apparatus of claim 1, further comprising an input device configured to receive a selection of an image mode from a user,
wherein the image processor is further configured to generate the contrast agent image when a first image mode is selected, and to generate the internal diagnostic image when a second image mode is selected.

12. The ultrasound imaging apparatus of claim 1, wherein the contrast agents comprise a shell composed of the silica nanostructure, and a core composed of a liquid perfluorocarbon or a gas perfluorocarbon.

13. The ultrasound imaging apparatus of claim 12, wherein
a size of the shell is equal to or greater than 10 nanometers and equal to or less than 3000 nanometers.

14. A control method of an ultrasound imaging apparatus comprising:
controlling an operation of a probe to irradiate focused ultrasound energy when contrast agents composed of a silica nanostructure are injected into an object,
controlling the operation of the probe to irradiate diagnostic ultrasound energy when the focused ultrasound energy is irradiated,
controlling the operation of the probe so that echo ultrasound energy reflected from the object is received when the diagnostic ultrasound energy is irradiated,
generating a Cadence Pulse Sequencing mode (CPS-mode) image as a contrast agent image and a Brightness mode (B-mode) image as an internal diagnostic image based on a received electrical signal corresponding to the echo ultrasound energy,
extracting pixels having brightness more than a predetermined threshold from the CPS-mode image, and
combining the extracted pixels with the B-mode image.

* * * * *